United States Patent [19]

Solar et al.

[11] Patent Number: 4,917,666
[45] Date of Patent: Apr. 17, 1990

[54] STEERABLE THRU-LUMEN CATHETER

[75] Inventors: Ronald J. Solar; Leo Roucher, both of San Diego, Calif.

[73] Assignee: Medtronic Versaflex, Inc., San Diego, Calif.

[21] Appl. No.: 270,557

[22] Filed: Nov. 14, 1988

[51] Int. Cl.⁴ ............................................. A61M 25/00
[52] U.S. Cl. ......................................... 604/95; 604/96; 606/194
[58] Field of Search ...................... 604/93, 95, 96–103, 604/344, 325, 348.1, 282, 657

[56] References Cited

U.S. PATENT DOCUMENTS

| | | | |
|---|---|---|---|
| 4,044,765 | 8/1977 | Kline | 604/164 |
| 4,307,722 | 12/1981 | Evans | 128/344 |
| 4,571,240 | 2/1986 | Sampson et al. | 604/96 |
| 4,646,719 | 3/1987 | Neuman et al. | 128/344 |
| 4,723,936 | 2/1988 | Buchbinder et al. | 128/344 |
| 4,733,652 | 3/1988 | Kantrowitz et al. | 604/96 |

Primary Examiner—Stephen C. Pellegrino
Attorney, Agent, or Firm—John L. Rooney; Hugh D. Jaeger

[57] ABSTRACT

This invention relates to steerable thru-lumen catheters and a method of using same, especially in the cardiovascular field. More particularly, this invention relates to a dilatation catheter means comprising:

a first flexible tubular member comprising a spring coil body defining a lumen, said spring coil body having a flexible covering thereon, a second, smaller, tubular member having one or more lumens, at least one of which lumens is open at its distal end, said second tubular member extending through said first tubular member such that the distal end of said second tubular member extends distally to the distal end of said first tubular member, dilatation balloon means positioned concentric to the distal ends of said first and second catheter means, and control means attached to the proximal end of said dilatation catheter, the control means having at least one passageway in fluid connection with the interior of said first tubular member and/or one or more lumens of said second tubular member, the control means and the dilatation catheter being so configured that when the control means is rotated, the dilatation catheter itself rotates to cause the distal end of the dilatation catheter to rotate.

22 Claims, 3 Drawing Sheets

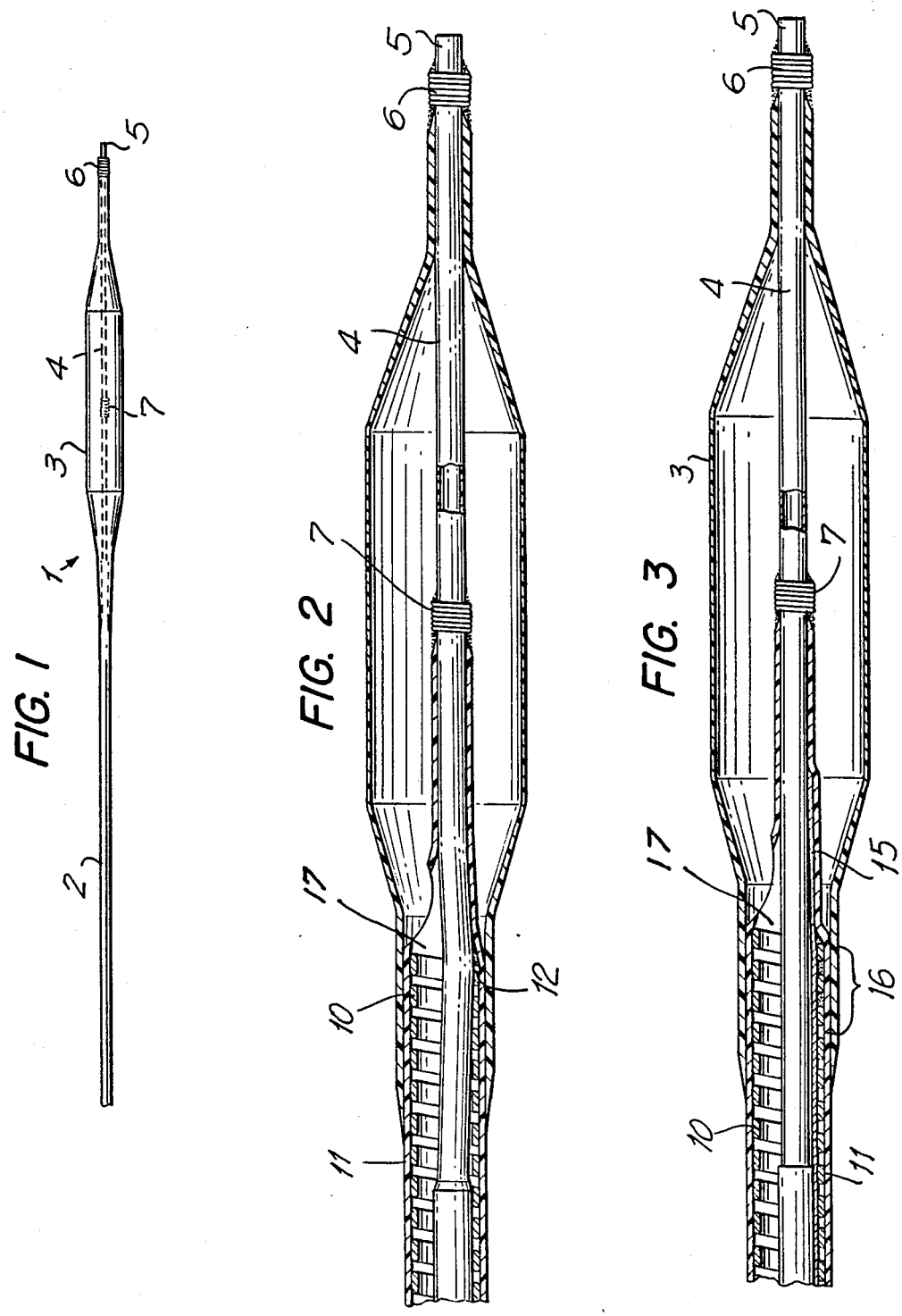

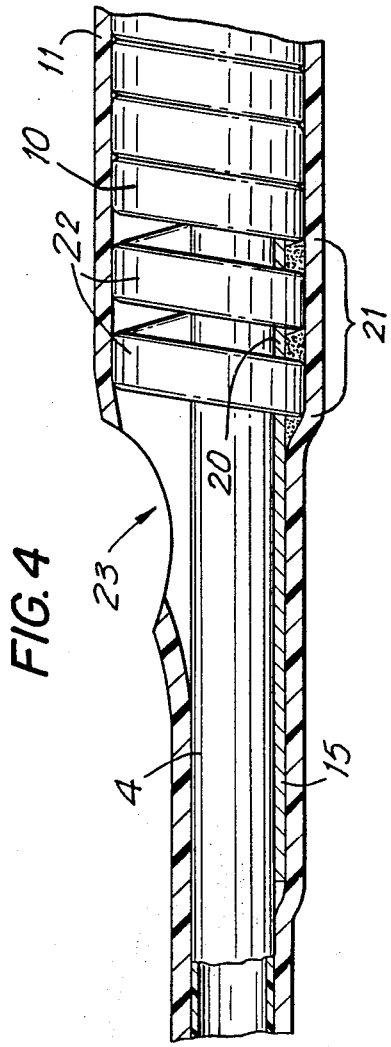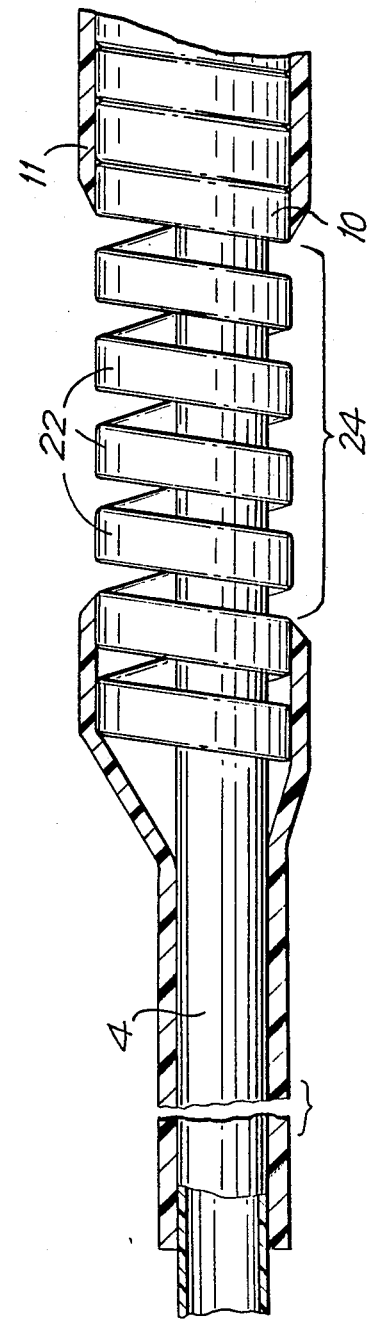

STEERABLE THRU-LUMEN CATHETER

FIELD OF THE INVENTION

This invention relates to a steerable catheter. More particularly, this invention relates to steerable thru-lumen catheters and a method of using same, especially in the cardiovascular field.

BACKGROUND OF THE INVENTION

Catheters comprise tube-like members that are inserted into the body for various medical reasons, some diagnostic and others therapeutic. While in many instances the steerability or directionality of such catheters is of concern, steerability is particularly important with regard to certain urological or cardiovascular applications.

There have been various attempts to develop steerable catheters. For example, U.S. Pat. No. 1,060,665 describes an early attempt to provide a catheter capable of some direction. However, the device disclosed in this patent, as well as catheters and catheter guides disclosed in later patents, such as U.S. Pat. Nos. 2,574,840 and 2,688,329 tend to be characterized by only limited directionality.

In addition, some supposedly steerable catheters are too large and rigid to be of practical use in cardiovascular techniques. See, for example, U.S. Pat. Nos. 3,470,876 and 3,605,7225, where wires equidistantly positioned along the length of a catheter are connected to a steering means which pulls on the wires to cause the distal end of the catheter to go in a desired direction. Moreover, U.S. Pat. Nos. 3,521,620, 3,547,103, 3,625,200, and 4,020,829 describe coil spring guide wires that have a certain degree of directionality but are too rigid for safe usage in certain delicate cardiovascular procedures.

According to U.S. Pat. No. 4,033,331, a coronary catheter has a main lumen and a shaping wire lumen. When the wire is withdrawn through the shaping wire lumen, the catheter assumes certain predetermined configurations. While this so-called steerable catheter is useful in some cardiovascular applications, such as positioning the initial guiding catheter guide through which other devices are guided, its limited directionality and limited tip control preclude extensive use.

A medical procedure known as percutaneous transluminal coronary angioplasty (PTCA) was developed in approximately 1976–1977 by Dr. Andreas Gr'‚uml/u/ ntzig. According to this procedure, blockage in a coronary artery can be reduced by positioning a balloon dilatation catheter across the blockage and the inflating the balloon, which causes the blockage to decrease. Such positioning requires that the balloon dilatation catheter be "steered" into place, that is, across the stenotic lesion causing the blockage, by manipulation at the proximal end of the catheter.

The procedure is actually somewhat complex, consisting of introducing a catheter system via the femoral or brachial artery under local anesthesia. A pre-shaped guiding catheter is positioned into the orifice of the coronary artery, and through this guiding catheter a second dilatation catheter is advanced into the branches of the coronary artery. The dilatation catheter has an elliptically shaped balloon portion near the tip which can be inflated and deflated. After traversal of the stenotic lesion of the coronary artery, the balloon portion is inflated with fluid, which dilates the lumen of the vessel.

The PTCA procedure and equipment have become increasingly refined over the past six years. The first marketable PTCA apparatus consisted of a small catheter with a single balloon port and no central lumen, that is, a socalled "fixed wire" system, which terminated in lateral openings at the distal end thereof. This system, which is the subject of U.S. Pat. No. 4,195,637, was designed by Dr. Grüntzig and was marketed in the U.S. by USCI. The fixed wire catheter system disclosed in U.S. Pat. No. 4,195,637 comprises a balloon dilatation catheter and a low friction guide catheter consisting of one tubular member fitted into a more rigid, shrunk-on tubular member that is not co-extensive. The distal end of the balloon dilatation catheter has a flexible tip advantageously fabricated from a spring steel wire.

In 1980–1981 Dr. John Simpson, working at Stanford University, began to modify the fixed wire system and eventually developed a catheter with a free central lumen for movable guide wires. This catheter system is the subject of U.S. Pat. No. 4,323,071, which is assigned to Advanced Cardiovascular Systems, Inc. (ACS), formerly known as Advanced Catheter Systems, Inc. By use of such a movable wire system, one could more readily select the desired coronary artery and reach smaller branches since the movable guide wires are inherently smaller and more flexible than the fixed wire system. Subsequent to the development of the catheter with movable guide wires, known as the Simpson-Robert system and marketed by ACS, USCI has abandoned the fixed wire system and has marketed a similar device, calling it the steerable catheter, DILACA ®.

There is a further catheter system in use known as the Hartzler low profile catheter system. According to this catheter system a balloon dilatation catheter has a concentrically contained guide wire extending the length of said catheter. Moreover, the distal end of the guide wire extends a short distance beyond the distal end of the balloon dilatation catheter and is affixed to the distal end of the balloon dilatation catheter.

The catheter system with movable guide wires and the low profile catheter system each represent an advance but still have disadvantages such as limited steerability, which is at present dependent upon the torquability, or torque control, of the movable wire. Steerability is highly significant in a cardiovascular procedure such as PTCA, or angioplasty, because less steerability results in greater time spent in the body and more possible patient trauma. Multiple insertions of guide wires and catheters can lead to thrombosis in that coagulation may commence along a guide wire surface and be forced into the heart when a catheter is slid over the guide wire. Furthermore, there are some blockages which simply can't be reached with presently known equipment.

There has been a need for more steerable catheter means, especially means useful in a procedure such as PTCA. Preferably such catheter means should have the following characteristics:

1. The entire catheter should be small enough to compare favorably with the already existing small dilatation catheters.

2. The catheter should be capable of rotational and deflective movement. Rotational movement of the steering tip should be precise enough to provide as close to 1:1 torque as possible. This would make the device very useful since it could ultimately be substituted for high torque wires already available.

U.S. Pat. application Ser. No. 193,201, filed May 19, 1988, U.S. Pat. application Ser. No. 48,550, filed May 12, 1987, and U.S. Pat. application Ser. No. 213,662, filed June 30, 1988, all of which are incorporated herein by reference, are directed to improved steerable catheter means useful in, for example, cardiovascular applications. The catheter means disclosed therein are characterized by a relatively low profile and enhanced directionality due to combined rotation of the catheter means and active deflection of the catheter tip.

OBJECTS OF THE INVENTION

It is an object of the invention to provide a steerable catheter.

It is also an object of the invention to provide a steerable thru-lumen catheter useful in cardiovascular applications.

It is a further object of the invention to provide a delivery means and a method of using said delivery means to deliver objects such as guidewires or balloons to various parts of the cardiac and vascular systems as well as of the body.

It is a yet further object of the invention to provide a dilatation catheter means comprising:

a first flexible tubular member comprising a spring coil body defining a lumen, each of said first tubular member and said spring coil body having proximal and distal ends, and said spring coil body having a flexible covering thereon, a second, smaller tubular member having distal and proximal ends and having one or more lumens, at least one of which lumens is open at its distal end, said second tubular member extending through said first tubular member such that the distal end of said second tubular member extends distally to the distal end of said first tubular member, dilatation balloon means positioned concentric to the distal ends of said first and second tubular members, and control means attached to the proximal end of said dilatation catheter, the control means having at least one passageway in fluid connection with the interior of said first tubular member and/or one or more lumens of said second tubular member, the control means and the dilatation catheter being so configured that when the control means is rotated, the dilatation catheter itself rotates to cause the distal end of the dilatation catheter to rotate.

These and other objects of the invention will become more apparent in the discussion below.

BRIEF DESCRIPTION OF THE DRAWINGS

FIG. 1 represents a plan view of the distal section of an embodiment of the invention;

FIGS. 2 and 3 each represent a partly cross-sectional view of the distal portion of an embodiment of the invention;

FIGS. 4 and 5 each represent a partly cross-sectional view of a proximal portion of an embodiment of the invention.

DETAILED DESCRIPTION OF THE INVENTION

Figure 6:
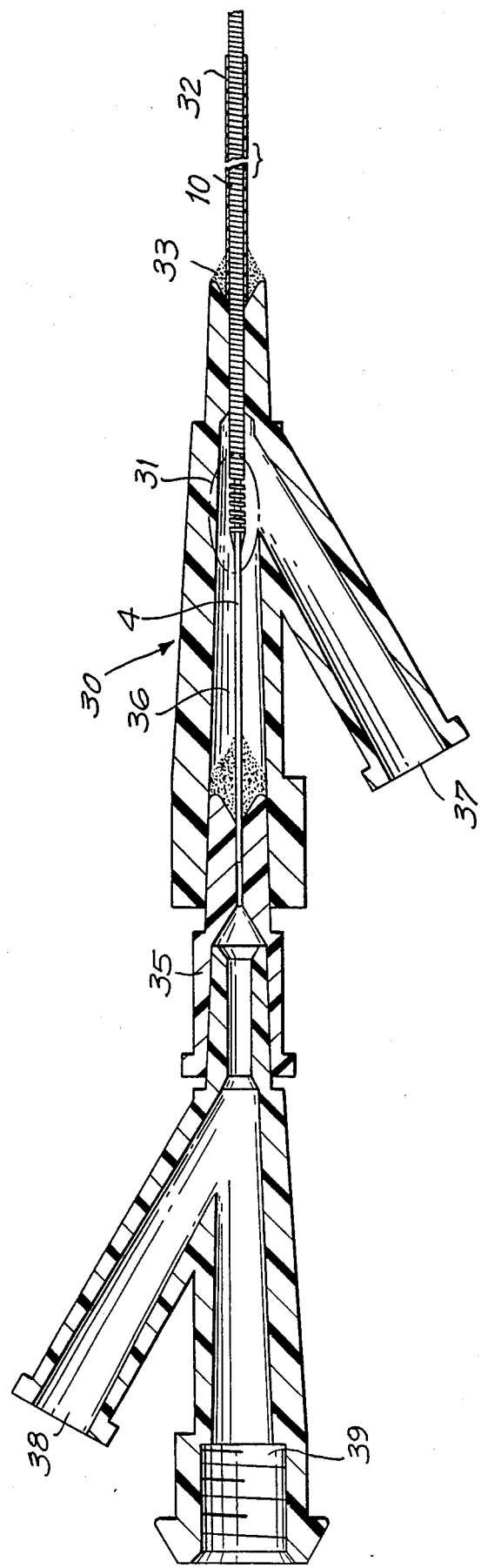
FIG. 6 represents a plan view of the proximal section of an embodiment of the invention.

Applicants have, surprisingly developed a flexible dilatation catheter means having advantageous characteristics. According to the invention, a dilatation catheter means comprising:

a first flexible tubular member comprising a spring coil body defining a lumen, each of said first tubular member and said spring coil body having proximal and distal ends, and said spring coil body having a flexible covering thereon, a second, smaller tubular member having distal and proximal ends and having one or more lumens, at least one of which lumens being open at its distal end, said second tubular member extending through said first tubular member such that the distal end of said second tubular member extends distally to the distal end of said first tubular member, dilatation balloon means positioned concentric to the distal ends of said first and second tubular members, and control means attached to the proximal end of said dilatation catheter, the control means having at least one passageway in fluid connection with the interior of said first tubular member and/or one or more lumens of said second tubular member, the control means and the dilatation catheter being so configured that when the control means is rotated, the dilatation catheter itself rotates to cause the distal end of the dilatation catheter to rotate.

In another embodiment of the invention, an anchor or torque wire may extend from the proximal end of the spring coil body through the first tubular member to a point within the dilatation balloon. Preferably this torque wire is attached, such as by adhesive, solder, a weld, or a braze, to the interior surface of each of the proximal and distal ends of the spring coil body. It is especially preferred that said torque wire gradually taper at its distal end, said tapering starting approximately 8 to 20 cm, preferably 10 to 12 cm, proximal to its distal end.

The second tubular member may comprise one or more lumens; at least one of the lumens is open at its distal end. Preferably, the second tubular member comprises a single, open lumen that is in fluid communication with a passageway in the control means. It is within the scope of the invention that when the second tubular member is a single lumen, this tubular member may comprise two or more members, preferably two members of dissimilar size. For example, the second tubular member may comprise a first, larger member extending from the proximal end of the tubular member to a point within the dilatation balloon or adjacent to the proximal end thereof, where the proximal end of a second smaller member would be bonded to the inside of the distal end of the larger first member. Bonding could be accomplished by a U.V. curing adhesive or a cyano-acrylate bond.

The above-mentioned two-member arrangement for the second tubular member is suitable for certain polymeric materials, such as polyimide. However, preferably the second tubular member comprises a suitable polymeric material, such as polyethylene, that can be "necked down", or drawn, to reduce the diameter of the distal portion of the second tubular member. The reduction would occur about 8 to 20 cm, preferably 10 to 12 cm, proximal to the distal end of the second tubular member.

The invention can perhaps be better understood by making reference to the drawings. In FIG. 1, balloon dilatation catheter 1 has a first tubular member 2 which terminates proximal to a dilatation balloon 3. Extending the length of first tubular member 2, through dilatation balloon 3, is a second tubular member 4. Adjacent to the distal end 5 of second tubular member 4 is a radiopaque marker 6, and another radiopaque marker 7 is positioned within dilatation balloon 3 concentric to second tubular member 4. Markers 6 and 7, both of which are optional, may be comprised of radiopaque materials selected from the group consisting of platinum, gold, tungsten, and tantalum.

The structure of the distal portion of a catheter according to the invention can be seen much more clearly in FIGS. 2 and 3. It can be seen that the first tubular member 2 shown in FIG. 1 comprises spring coil body 10 having a flexible coating 11 thereon. Coating 11 extends over the entire exterior surface of spring coil body 10 and then terminates at a point distal to the distal end 12 of spring coil body 10, the coating being hermetically sealed to second tubular member 4. In the embodiment shown in FIGS. 2 and 3, the coating 11 is sealed to second tubular member 4 at the point where marker 7 is affixed to second tubular member 4. However, coating 11 could optionally extend further distally, even to the distal end 5 of second tubular member 4.

Coating 11, an impervious body skin or tubing, may comprise one or more layers of suitable low friction polymeric material such as a polyolefin, a polytetrafluoroethylene such as TEFLON ®, polyvinyl chloride, or the like, and may be applied by any one of a variety of methods known to those skilled in the art. For example, heat shrinkable tubing may be heat shrunk onto the spring coil body 10; polymeric material may be sprayed on or coextruded; or a tube of body skin may simply be slid over the spring coil body 10. Heat shrinking heat shrinkable tubing is preferred.

The proximal end of dilatation balloon 3 is attached to the spring coil body 10 and/or coating 11 at a point adjacent to the distal end of spring coil body 10. The distal end of dilatation balloon 3 is attached to the distal portion of second tubular member 4. The proximal and distal portions of dilatation balloon means can be attached by means known to those skilled in the art, such as adhesive bonding, heat shrinking, or the like. It is within the scope of the invention that coating 11 and dilatation balloon 3 could alternately comprise a single, integral member.

Materials suitable for dilatation balloons are well known. For example, polyethylene or copolymers thereof are especially useful in this regard.

Dilatation balloon 3 can be inflated, and deflated, through an opening or skive 17 in coating 11. In another embodiment of the invention not depicted here, there could be a space between coating 11 and spring coil body 10 through which fluid would flow. Suitable inflation fluids, such as saline solution or contrast fluid, are well known to those skilled in the art.

Spring coil body 10 substantially comprises tightly wound coils. However, preferably the distal portion of spring coil body 10, from about 5 to 35 cm, more preferably from about 10 to 30 cm, of the distal portion, comprises loosely wound coils having, for example, from about 0.001 to 0.005 in. between coils. In an especially preferred embodiment, approximately 30 cm of the distal spring coil body 10 are more loosely wound.

Optional torque wire 15, which is bonded to the spring coil body 10 at its proximal and distal ends, for example, at contact point 16, may be made from any metal wire, preferably a high tensile strength circular wire of stainless steel having a diameter of from about 0.001 to 0.020 in. Optionally this wire may have a rectangular cross-section of from about 0.001 to 0.020 in. × from about 0.001 to 0.040 in. Regardless of the shape of the cross-section, the distal end of torque wire 15 may be tapered, for example, to a diameter of from about 0.001 to 0.010. Also, the distal portion of torque wire 15 can be bonded by suitable means, e.g., mechanical means, adhesive, solder, braze, or weld, to the interior surface of spring coil body 10.

The proximal portion of spring coil body 10 is shown in each of FIGS. 4 and 5. In the embodiment of the invention shown in FIG. 4, the proximal distal portion 20 of torque wire 15 is bonded to spring coil body 10 at contact point 21. Optionally proximal portion 20 of torque wire 15 may extend proximally to contact point 21, said proximal portion 20 fitting between coating 11 and second tubular member 4.

It is preferred that from about 1 to 20 mm, more preferably from about 2 to 10 mm, of the proximal coils 22 of spring coil body 10 are more loosely wound.

Coating 11 may have one or more openings 23 to facilitate fluid flow for inflation and/or deflation of dilatation balloon 3. In FIG. 5 coating 11 is wholly or substantially discontinuous at discontinuity 24 to permit inflation and/or deflation of dilatation balloon 3. Discontinuity 24 corresponds substantially to the extent of the looser wound coils 22.

A typical control means 30 is shown in FIG. 6. Spring coil body 10 terminates at highlighted area 31, which area is effectively depicted in FIG. 4 or 5. An optional outer polymeric tubular member 32 may extend over the proximal portion of spring coil body 10 from a point approximately 5 to 25 cm distal of the control means 30 to fixation area 33, where the outer tubular member 32 is affixed to control means 30, preferably by adhesive bonding.

Second tubular member 4 extends proximally to engaging member 35, where it is affixed by adhesive or other suitable bonding means. Coating 11 may extend proximally from highlighted area 31 to engaging member 35. Engaging member 35 is slidably and/or rotatably fixed, or merely fixed, in a sealing manner within chamber 36. Port 37 facilitates inflation/deflation of dilatation balloon 3, and port 38 facilitates insertion of a guidewire (not shown). Opening 39 normally receives a molded hub (not shown).

Spring coil body 10 may be comprised of flat or round metal wire or plastic coil and may comprise one continuous coil or two or more, preferably 2 or 3, coil sections that are jointed together. For example, a reduced tension section could comprise a radiopaque material. Preferably spring coil body 10 is comprised of stainless steel flat wire having a cross-sectional width of from about 0.001 to 0.005 in., more preferably from about 0.002 to 0.004 in., and a crosssectional length of from about 0.007 to 0.013 in., more preferable from about 0.008 to 0.012 in. A spring coil body 10 made from a flat, i.e., rectangular, stainless steel wire is preferred, typical dimensions of the coil being from about 0.002 to 0.500 in. i.d., from about 0.004 to 0.750 in. o.d., and from about 12 to 72 in. in length.

In another embodiment of the invention, not shown, the distal portion of a primary coil of spring coil body 10 extending distally from a control means may terminate at a point substantially immediately proximal to the proximal portion of dilatation balloon 3, and then a second, smaller coil would extend from the distal end of the primary coil to distal end of spring coil body 10. The proximal end of the second, smaller coil would be bonded by suitable means to the interior of the distal portion of the primary coil. The second coil, which may be comprised of flat or round wire, is preferably comprised of round wire having a diameter of from about 0.001 to 0.020 in. The second coil may be uniformly wound or the distal portion thereof may be more loosely wound.

The use of guidewires and balloon dilatation catheters in performing PTCA is well known to those skilled in the art. Reference can be made to the aforementioned patents and patent applications, as well as U.S. Pat. No. 4,723,936, all of which are incorporated herein by reference.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A dilatation catheter means comprising:
   a first flexible tubular member having proximal and distal ends comprising a spring coil body defining a lumen, said spring coil body having proximal and distal ends, and a flexible covering positioned over said spring coil body,
   a second, smaller tubular member having distal and proximal ends and having at last one lumen, wherein at least one of said at least one lumen is open at its distal end, said second tubular member extending through said first tubular member such that the distal end of said second tubular member extends distally beyond the distal end of said first tubular member,
   dilatation balloon means attached concentric to the distal ends of said first and second tubular members, and
   control means attached to the proximal end of said dilatation catheter, the control means having at least one passageway in fluid connection with the interior of said first tubular member and/or one more lumens of said second tubular member, the control means and the dilatation catheter being so configured that when the control means is rotated, the dilatation catheter itself rotates to cause the distal end of the dilatation catheter to rotate.

2. The catheter means of claim 1, wherein the proximal end of the dilatation balloon means is joined to the distal end of said first tubular member and the distal end of the balloon dilatation balloon means is joined to said second tubular member at a point adjacent to or proximal to the distal end of said second tubular member.

3. The catheter means of claim 1, wherein there is spacing between the flexible covering and said spring coil body sufficient to facilitate inflation of the dilatation balloon.

4. The catheter of claim 1, wherein a marker comprised of radiopaque material is positioned within said dilatation balloon.

5. The catheter of claim 1, wherein a marker comprised of radiopaque material is positioned distal to the dilatation balloon.

6. The catheter means of claim 1, wherein the flexible covering comprises a flexible polymeric material.

7. The catheter means of claim 6, wherein the flexible polymeric material is polytetrafluoroethylene, polyethylene, or polyvinyl chloride.

8. The catheter means of claim 1, wherein the spring coil body comprises two or more spring coils.

9. The catheter means of claim 8, wherein the spring coil body comprises two spring coils having respective smaller and larger diameters, the proximal end of the spring coil with the smaller diameter being bonded to the inside of the distal end of the spring coil with the larger diameter.

10. The catheter means of claim 1, wherein said second tubular member comprises two or more members.

11. The catheter means of claim 10, wherein said second tubular member comprises two members having respective smaller and larger diameters, the proximal end of the member with the smaller diameter being bonded to the inside of the distal end of the member with the larger diameter.

12. The catheter means of claim 1, wherein the distal portion of said second tubular member is reduced in diameter.

13. The catheter of claim 1, wherein a marker comprised of radiopaque material is positioned distal to the distatation balloon.

14. A dilatation catheter means comprising:
    a first flexible tubular member having proximal and distal ends comprising a spring coil body defining a lumen, said spring coil body having proximal and distal ends, and a flexible covering positioned over said spring coil body,
    a second, smaller tubular member having distal and proximal ends and having a single lumen open at its distal end, said second tubular member extending through said first tubular member such that the distal end of said second tubular member extends distally beyond the distal end of said tubular member,
    a dilatation balloon means positioned concentric to the distal ends of said first and second tubular members, the proximal end of the dilatation balloon means being joined to the distal end of said first tubular member and the distal end of the balloon dilatation balloon means being joined to said second tubular member at a point adjacent to or proximal to the distal end of said second tubular member, and
    control means attached to the proximal end of said dilatation catheter, the control means having one passageway in fluid connection with the interior of said first tubular member and a second passageway in fluid communication with the lumen of said second tubular member, the control means and the dilatation catheter being so configured that when the control means is rotated, the dilatation catheter itself rotates to cause the distal end of the dilatation catheter to rotate.

15. The catheter of claim 14, wherein a marker comprised of radiopaque material is positioned distal to the dilatation balloon.

16. The catheter means of claim 13, wherein the flexible covering comprises a flexible polymeric material.

17. The catheter means of claim 16, wherein the flexible polymeric material is polytetrafluoroethylene, polyethylene, or polyvinyl chloride.

18. The catheter means of claim 13, wherein the spring coil body comprises two or more spring coils.

19. The catheter means of claim 18, wherein the spring coil body comprises two spring coils having respective smaller and larger diameters, the proximal end of the spring coil with the smaller diameter being bonded to the inside of the distal end of the spring coil with the larger diameter.

20. The catheter means of claim 13, wherein said second catheter means comprises two or more members.

21. The catheter means of claim 20, wherein said second tubular member comprises two members having respective smaller and larger diameters, the proximal end of the member with the smaller diameter being bonded to the inside of the distal end of the member with the larger diameter.

22. The catheter means of claim 13, wherein the distal portion of said second tubular member is reduced in diameter.

* * * * *

UNITED STATES PATENT AND TRADEMARK OFFICE
CERTIFICATE OF CORRECTION

PATENT NO. : 4,917,666

DATED : April 17, 1990

INVENTOR(S) : Ronald J. Solar, etal

It is certified that error appears in the above-identified patent and that said Letters Patent is hereby corrected as shown below:

At column 1, line 51, "Gr',uml/u/ntzig" should read: "Gruntzig"; and

At column 8, lines 21 and 22, "distal to the distation" should read: "Within said dilatation".

Signed and Sealed this

Eighth Day of December, 1992

Attest:

DOUGLAS B. COMER

Attesting Officer

Acting Commissioner of Patents and Trademarks